United States Patent [19]

Kensey

[11] Patent Number: 5,041,124

[45] Date of Patent: Aug. 20, 1991

[54] APPARATUS AND METHOD FOR SCLEROSING OF BODY TISSUE

[75] Inventor: Kenneth Kensey, Chester Springs, Pa.

[73] Assignee: Kensey Nash Corporation, Exton, Pa.

[21] Appl. No.: 380,930

[22] Filed: Jul. 14, 1989

[51] Int. Cl.⁵ .............................................. A61B 17/32
[52] U.S. Cl. ................................. 606/170; 15/104.14
[58] Field of Search ................ 128/751, 898; 606/159, 606/170; 604/22; 15/72, 104.14

[56] References Cited

U.S. PATENT DOCUMENTS

| | | | |
|---|---|---|---|
| 962,370 | 6/1910 | Malick | 15/104.14 |
| 1,837,904 | 12/1931 | Hanelt | 15/104.14 |
| 2,838,779 | 6/1958 | Craig et al. | 15/104.14 |
| 3,730,185 | 5/1973 | Cook et al. | 606/159 |
| 3,996,637 | 12/1976 | Shibata et al. | 15/104.14 |
| 4,686,982 | 8/1987 | Nash . | |
| 4,732,154 | 3/1988 | Shiber | 606/159 |
| 4,795,438 | 1/1989 | Kensey et al. | 606/159 |
| 4,811,735 | 3/1989 | Nash . | |

Primary Examiner—Stephen C. Pellegrino
Assistant Examiner—William W. Lewis
Attorney, Agent, or Firm—Caesar, Rivise, Bernstein, Cohen & Pokotilow, Ltd.

[57] ABSTRACT

A method and apparatus for sclerosing tissue located within an organ, e.g., the gall bladder, of a living being. The apparatus comprises a catheter having a rotatable working head at its distal end. The working head includes an extendable tissue engaging member. The catheter is introduced percutaneously through an introducer sleeve so that the working head is located within the organ. The extendable member is extended generally outward radially when the working head is rotated at a high rate of speed to cause its free end to repeatedly engage the tissue forming an inner surface of the organ to thereby mechanically scrape that tissue. A sclerosing agent, e.g., alcohol, may also be introduced into the organ to expedite the procedure.

17 Claims, 2 Drawing Sheets

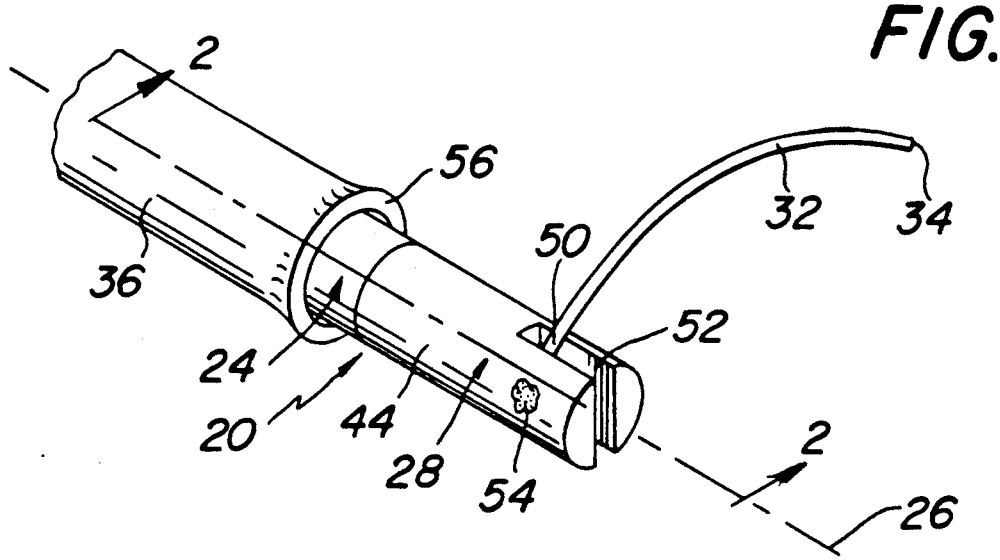
FIG. 1
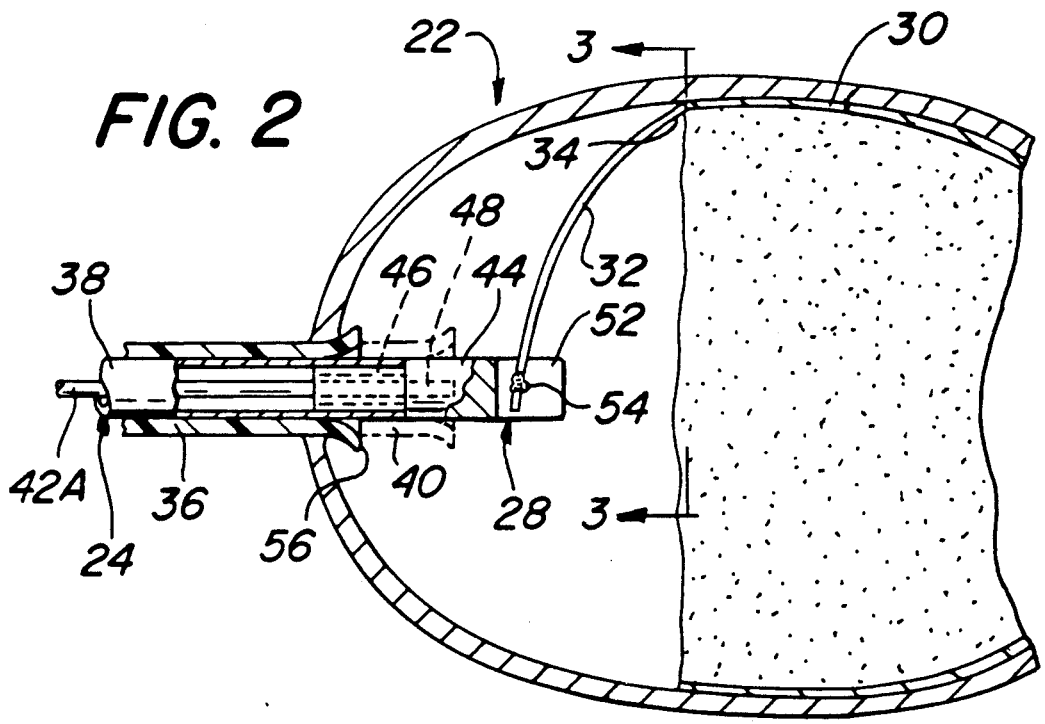
FIG. 2
FIG. 3

APPARATUS AND METHOD FOR SCLEROSING OF BODY TISSUE

SPECIFICATION

This invention relates generally to apparatus and a method for mechanically sclerosing internal body tissue and more particularly to apparatus and a method for sclerosing the mucosa of the gall bladder.

BACKGROUND OF THE INVENTION

In U.S. Pat. No. 4,811,735, entitled Stone Destroying Catheter and Method of Use, and in a copending U.S. patent application Ser. No. 07/322,754, filed on Mar. 13, 1989, entitled Stone Pulverizing Apparatus with Improved Working Head and Method of Use, both of which are assigned to the same assignee as this invention, and whose disclosures are incorporated by reference herein, there are disclosed and claimed apparatus and methods for destroying stones with minimum invasion of the body. Thus, such devices and methods of use for performing a cholecystotomy entail the percutaneous introduction of an instrument, e.g., a catheter, into the gall bladder. The catheter includes a rotatable working head having extendable blades. The head is rotated at a high rate of speed about the longitudinal axis of the catheter. This action creates a vortex flow in the liquid within the gall bladder to carry the stones into engagement with the blades of the working head, whereupon the stones are repeatedly impacted and pulverized.

As will be appreciated by those skilled in the art it is frequently desirable to perform a cholecystotomy, i.e., removal of the gall bladder, to thereby prevent the reformation of such stones. Thus, when the apparatus and methods of the aforementioned patent and patent application are used to perform a percutaneous cholecystotomy, it may also be desirable to remove or render inoperative the patient's gall bladder. Since the apparatus and methods of the aforementioned patent and patent application effect stone destruction with minimum invasion of the patient's body, by virtue of the percutaneous insertion and operation of the small diameter catheter it would be counterproductive to perform a cholecystotomy using conventional surgical techniques. By sclerosing or denuding the mucosa (inner lining) of the gall bladder with some minimally invasive procedure, the gall bladder will shrink and/or become necrotic and be absorbed by the patient's body thereby achieving the end result of a conventional surgical cholecystotomy without surgery.

OBJECTS OF THE INVENTION

Accordingly, it is the general object of this invention to provide apparatus and methods for sclerosing body tissue with minimal invasion of the body.

It is a further object of this invention to provide a small percutaneously inserted instrument which is simple in construction and easy to use for sclerosing interior body tissue.

It is still a further object of this invention to provide a catheter based instrument and method of use for effecting percutaneous cholecystectomies.

SUMMARY OF THE INVENTION

These and other objects of the instant invention are achieved by providing a method and apparatus for sclerosing tissue located within an organ, e.g., the gall bladder, in the body of a living being. The apparatus comprises a small diameter, elongated body with a movable working head at its distal end. The apparatus is introduced into the body of the being so that it's working head is located within the organ at the situs of the tissue to be sclerosed. The working head includes a free end portion arranged to be extended generally outward radially. The working head is rotated at a high rate of speed with the free end portion extended. The rotating free end portion is brought into engagement with the tissue forming an inner surface of the organ to mechanically denude that tissue. In accordance with one aspect of the invention the apparatus comprises a catheter which is percutaneously inserted into the organ via an introducer sleeve.

DESCRIPTION OF THE DRAWINGS

Other objects and many of the attendant advantages of this invention will be readily appreciated as the same becomes better understood by reference to the following detailed description when considered in connection with the accompanying drawings wherein:

FIG. 1 is a perspective view of the distal end of an apparatus constructed in accordance with one aspect of this invention and for carrying out the method of this invention;

FIG. 2 is a side elevational view, partially in section, taken along line 2—2 of FIG. 1 showing the apparatus of FIG. 1 in place within a gall bladder for denuding its mucosa;

FIG. 3 is a sectional view taken along line 3—3 of FIG. 2;

DETAILED DESCRIPTION OF THE PREFERRED EMBODIMENT

Figure 4:
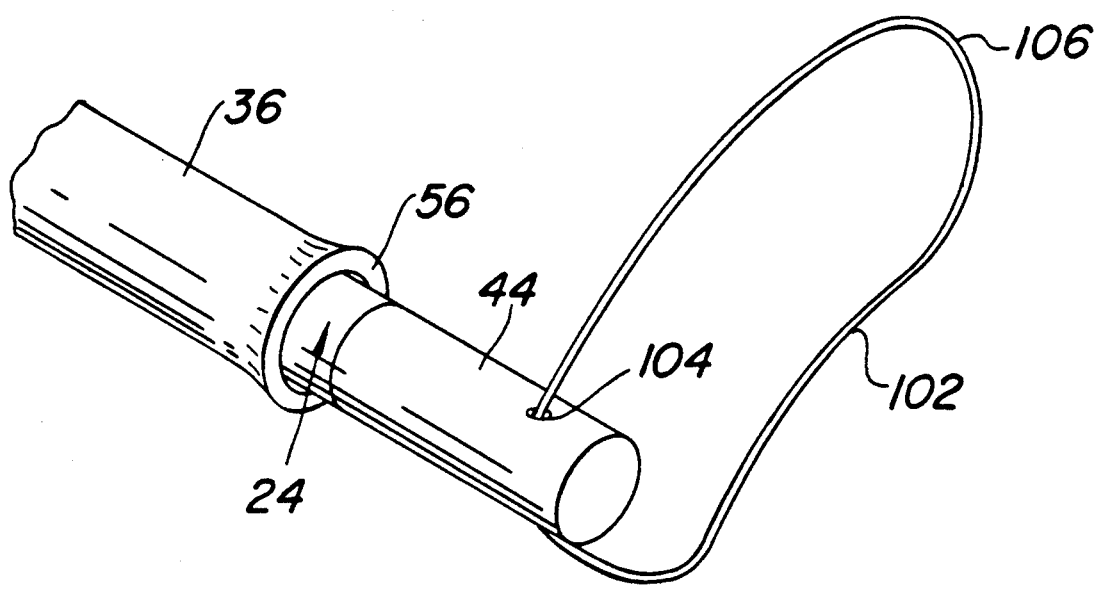
FIG. 4 is a perspective view similar to that of FIG. 1 but showing an alternative embodiment of the apparatus of this invention.
Figure 5:
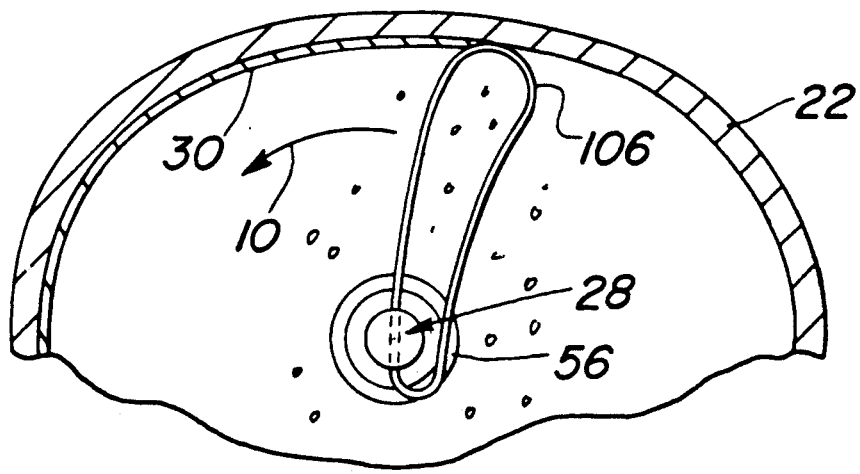
FIG. 5 is a sectional view similar to FIG. 3 showing the operation of the embodiment of the apparatus of FIG. 4.

Referring now in detail to the various figures of the drawing wherein like reference characters refer to like parts, there is shown at 20 in FIG. 1 apparatus constructed in accordance with the subject invention. That apparatus is arranged to be disposed within the gall bladder 22 (FIG. 2) or some other organ or lumen within the body of a living being to sclerose or denude it's tissue.

In one preferred aspect of this invention the apparatus 20 is used to perform a percutaneous cholecystectomy. Such a procedure may be conducted after gall stones have be destroyed by the use of the catheter-based instruments of the aforementioned patent and patent application owned by the assignee of this invention.

The apparatus 20 preferably comprises a small diameter catheter, having an elongated body portion 24 including a longitudinal central axis 26 and a rotatable working head 28 located at the distal end thereof. The elongated body portion is arranged to be introduced into the patient's body so that the apparatus' working 28 is located at the situs of the tissue to be sclerosed. Thus, when performing a cholecystectomy the catheter is preferably inserted percutaneously through the liver (not shown) and into the gall bladder 22 so that the working head 28 is within the interior of the gall bladder adjacent the mucosa 30 (FIG. 2).

The working head will be described in detail later. Suffice it for now to state that it basically comprises an elongated extendable member 32, which is arranged to be rotated at a high speed about the longitudinal axis 26 of the device 20 so that its free end portion 34 scrapes, denudes or otherwise scleroses the mucosa. Details of the catheter's body will also be described later. Suffice it to say that such a construction is merely exemplary. Thus, other suitable types of catheters can be used with the working head of this invention to perform the methods of this invention. In fact, the working head of this invention can be used with any instrument or device which is suitable for insertion into the body at the situs of the tissue to be sclerosed or denuded. Moreover, the methods of this invention may be carried out with other working heads than that disclosed herein.

The use of a flexible catheter as the means for introducing and operating the rotating working head does, however, offer the advantage of facilitating the placement of the working head at the desired location within the body. Thus, for example it enables percutaneous or other minimally invasive insertion techniques. The positioning of the catheter within the body at the desired operative situs may also be facilitated in any conventional manner, e.g., through the use of a conventional tubular introducer sleeve 36, which is first introduced percutaneously over a guide wire (not shown) and moved through the body to the desired position within the gall bladder. The distal end of the introducer sleeve is flared. That feature aids in holding the introducer in position.

As can be seen in FIG. 1 the catheter body basically comprises an elongated outer jacket 38 of small diameter, e.g., 7 French (23.6 mm). The working head 28 is mounted on the distal end of the body, via mounting means comprising a bearing 40. A drive system 42 is located within the jacket 38 and is connected to the working head 28 to effect the rotation of the working head at a high rate of speed, e.g., 10,000 to 100,000 RPM, about axis 26 in either rotational direction. In FIG. 3 the rotation of the working head in the counter-clockwise direction is shown by the direction of the arrow designated by the reference numeral 10. The rotating working head's extending member 34 may then be brought into engagement with the mucosa 30 to denude it.

The drive system 42 can take various forms, such as an elongated drive wire or cable 42A extending within the catheter's jacket 38 from a proximately located motor (not shown). Alternatively the drive means may be constructed in accordance with the teachings in U.S. Pat. No. 4,606,902 entitled Spiral Wire Bearing for Rotating Wire Drive Catheter, said patent being assigned to the same assignee as this invention, and whose disclosure is incorporated by reference herein.

The details of the working head 28 and its components will now be discussed. As can be seen in FIGS. 1 and 2, the working head basically comprises a base or hub 44. The hub 44 includes a proximally located cylindrical portion 46 extending into a central passageway in the bearing 40. The bearing 40 is fixedly secured at the distal end of the catheter's jacket 38 by means (not shown). The distal end of the drive cable 42A passes through the passageway in the bearing and is fixedly secured in a central bore 48 of the hub 44.

In accordance with one preferred embodiment of the invention the extendable member 32 of the working head 28, is in the form of a single, flexible filament. The filament 32 is secured to the hub 44 adjacent the distal end thereof. In particular the inner end 50 of the filament is located within a slot 52 at the free end of the hub 44. The filament is fixedly secured in the slot via a laser spot weld 54 or by some other securement means. The free end of the filament 32, designated by the reference numeral 34, constitutes the filament's working or tissue-engagement end.

In the embodiment shown herein the filament is formed of polyvinyl chloride (PVC) or any other suitable plastic and is quite flexible so that it can be folded or bent back to a retracted position (not shown) wherein it lies close to the hub 44 and the contiguous portion of the catheter's jacket 38 when the apparatus is inserted through the introducer sleeve 36 into the gall bladder or other organ to be sclerosed. The filament preferably has some resiliency so that when the distal end of the catheter is located within the gall bladder and free of the distal end 56 of the introducer sleeve 36 the filament 32 springs outward to a somewhat radially extended position like that shown in FIGS. 1-3. Alternatively, some means (not shown) may be used to extend the filament to that position.

Even if no means or mechanism is provided to extend the filament to the position shown in FIGS. 1-3, it will nevertheless assume that orientation upon operation of the catheter 20. In this regard upon the rotation of the working head about axis 26 the centrifugal force produced by that rotation causes the filament 32 to extend to the outward radially extended position shown in FIGS. 1-3. It is in this position that the portions of the filament contiguous with the free end 34 scrape across the mucosa 30 of the gall bladder to sclerose or denude it. At the same time that the working head is rotating the catheter may be reciprocated (extended and retracted) longitudinally along axis 26 with respect to the introducer sleeve 36 to insure that the rotating filament 32 scrapes across or scleroses a sufficiently large portion of the gall bladder's mucosa to insure the destruction of the gall bladder (e.g., its shrinkage and ultimate absorption by the body).

In FIG. 4 there is shown an alternative embodiment of the apparatus of this invention. That apparatus makes use of an alternative rotating working head, now designated by the reference numeral 100. The construction of working head 100 is in most respects identical to that of working head 28. Therefore, common components will be given the same reference numerals in the interest of simplicity and brevity. However, there is one major difference between working head 28 and working head 100 in that the latter utilizes an extending member in the form of a loop 102 of a flexible filament formed of the same material that is used to form filament 32 of FIGS. 1-3. As can be seen in FIG. 4 the loop 102 extends through a diametrically oriented hole 104 in the distal end of the hub 44.

As will be appreciated by those skilled in the art, the loop filament 102 operates in a similar manner to the single filament 32 when the hub 44 is rotated about the central axis 26 of the catheter, so that its double filament free end portion 106 engages and sweeps across the mucosa 30, to thereby denude or sclerose it.

While working heads as described heretofore have taken the form of flexible filaments, it should be pointed out that other types of extendable members can be used to scrape, denude or otherwise sclerose the mucosa or other body tissue. Thus, the extending member may be flail-like, rigid, bent, hinged or combinations thereof so long as some extending surface portion is capable of being swept or scraped across the tissue to be sclerosed as the working head is rotated.

In order to expedite the sclerosing action a liquid or some other sclerosing agent can be introduced through the apparatus 20, or by some other means, into the gall bladder 22. One such sclerosing agent can be alcohol.

Without further elaboration, the forgoing will so fully illustrate my invention that others may, by applying current or future knowledge, readily adopt the same for use under various conditions of service.

What is claimed is:

1. Apparatus for sclerosing tissue located within an organ in the body of a living being comprising a small diameter, elongated, flexible catheter configured for ready insertion through a small incision or puncture into the body of said being to the situs of said organ, said catheter having a longitudinal central axis and a movable working head located at the distal end thereof, said working head comprising a flexible member having a free end portion arranged to be extended generally outward radially from a retracted radial position with respect to said axis to an extended radial position with respect thereto when said apparatus is located within said organ, means for rotating said working head at a high rate of speed with said free end portion in said extended position, whereupon said free end portion engages tissue forming an inner surface of said organ to mechanically denude said tissue.

2. The apparatus of claim 1 wherein said working head comprises a flexible filament.

3. The apparatus of claim 2 wherein said means for rotating said working head comprises an elongated drive wire, and wherein said flexible filament is coupled to said drive wire.

4. The apparatus of claim 2 additionally comprising a small diameter sleeve member which extends percutaneously into said organ and through which said catheter passes.

5. The apparatus of claim 1 wherein said free end portion of said working head is moved to said extended radial position in automatic response to the rotation of said working head about said axis.

6. The apparatus of claim 5 wherein said working head comprises a flexible filament.

7. The apparatus of claim 6 wherein said means for rotating said working head comprises an elongated drive wire, and wherein said flexible filament is coupled to said drive wire.

8. The apparatus of claim 7 additionally comprising a small diameter sleeve member which extends percutaneously into said organ and through which said instrument passes.

9. A method of sclerosing tissue located within an organ in the body of a living being comprising introducing a small diameter elongated catheter into the body of said being, said catheter having a longitudinal central axis and a movable working head located at the distal end thereof, said working head comprising a free end portion arranged to be extended generally radially outward from a retracted radial position with respect to said axis to an extended radial position with respect thereto, positioning said member within said organ at the situs of the tissue to be sclerosed, extending said portion from said retracted radial position to said extended radial position and causing said working head to be rotated at a high rate of speed with said free end portion extended, bringing said rotating free end portion into engagement with tissue forming an inner surface of said organ to sweep thereacross to mechanically denude said tissue.

10. The method of claim 9 wherein said apparatus is introduced into the body of said being percutaneously.

11. The method of claim 10 wherein said organ comprises the gall bladder and wherein said tissue comprises the mucosa.

12. The method of claim 11 additionally comprising the steps of introducing a sclerosing agent into said gall bladder.

13. The method of claim 9 wherein said extendable member comprises a filament.

14. The method of claim 13 wherein said filament is flexible.

15. The method of claim 14 wherein said organ comprises the gall bladder and wherein said tissue comprises the mucosa.

16. A method of sclerosing the mucosa located within the gall bladder in the body of a living being comprising introducing apparatus having a small diameter elongated body with a movable working head at its distal end into the body of said being so that said working head is located within said gallbladder at the situs of the mucosa to be sclerosed, said working head including a free end portion arranged to be extended generally outward radially, causing said working head to be rotated at a high rate of speed with said free end portion extended, bringing said rotating free end portion into engagement with the mucosa to mechanically denude it.

17. The method of claim 16 additionally comprising the steps of introducing a sclerosing agent into said gall bladder.

* * * * *